(12) United States Patent
Bharat et al.

(10) Patent No.: US 10,898,728 B2
(45) Date of Patent: Jan. 26, 2021

(54) ADAPTIVE TREATMENT PLANNING FOR HYPERTHERMIA-ENHANCED RADIATION THERAPY

(71) Applicant: KONINKLIJKE PHILIPS N.V., Eindhoven (NL)

(72) Inventors: Shyam Bharat, Arlington, MA (US); Ajay Anand, Fishkill, NY (US); Robert Michael Staruch, Dallas, TX (US); Shriram Sethuraman, Lexington, MA (US); Vijay Parthasarathy, Lexington, MA (US); Ehsan Dehghan Marvast, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 242 days.

(21) Appl. No.: 15/769,078

(22) PCT Filed: Oct. 13, 2016

(86) PCT No.: PCT/EP2016/074609
§ 371 (c)(1),
(2) Date: Apr. 18, 2018

(87) PCT Pub. No.: WO2017/071965
PCT Pub. Date: May 4, 2017

(65) Prior Publication Data
US 2018/0304100 A1 Oct. 25, 2018

Related U.S. Application Data
(60) Provisional application No. 62/248,484, filed on Oct. 30, 2015.

(51) Int. Cl.
*A61N 5/10* (2006.01)
*A61N 7/02* (2006.01)
(Continued)

(52) U.S. Cl.
CPC .............. *A61N 5/1048* (2013.01); *A61F 7/00* (2013.01); *A61N 5/1031* (2013.01);
(Continued)

(58) Field of Classification Search
CPC .......... A61N 5/02; A61N 5/022; A61N 5/025; A61N 5/04; A61N 5/06; A61N 5/0613;
(Continued)

(56) References Cited

U.S. PATENT DOCUMENTS 8,016,757 B2 * 9/2011 Kaczkowski .......... A61B 5/015
374/117
8,222,616 B2 7/2012 Lu
(Continued)

FOREIGN PATENT DOCUMENTS

WO 2005107601 11/2005
WO 2010/040364 4/2010
(Continued)

OTHER PUBLICATIONS

Taschereau, et al., "Radiation Dosimetry of a Conformal Heat-brachytherapy Applicator"; Technology in Cancer Research and Treatment, vol. 3, No. 4, Aug. 1, 2004.
(Continued)

*Primary Examiner* — Anastasia Midkiff

(57) ABSTRACT

A method includes generating a hyperthermia heat plan for tissue of interest, generating a hyperthermia adapted radiation therapy plan for the tissue of interest, controlling a heat source (126) to deliver heat to the tissue of interest according to the hyperthermia heat plan, and controlling a radiation source of a radiation therapy system (100) to deliver radiation to the tissue of interest according to the hyperthermia adapted radiation therapy plan. A system includes a radiation treatment planner (124) configured to generate a hyperthermia adapted radiation therapy plan for the tissue of interest,
(Continued)

a radiation therapy system (100) configured to deliver radiation in accordance with the hyperthermia adapted radiation therapy plan, and a hyperthermia heat delivery system (126) configured to deliver heat in accordance with a hyperthermia plan.

24 Claims, 7 Drawing Sheets

(51) Int. Cl.
*A61F 7/00* (2006.01)
*A61N 5/06* (2006.01)

(52) U.S. Cl.
CPC ......... *A61N 5/1037* (2013.01); *A61N 5/1038* (2013.01); *A61N 5/1075* (2013.01); *A61N 7/02* (2013.01); *A61F 2007/0089* (2013.01); *A61F 2007/0095* (2013.01); *A61N 2005/0626* (2013.01); *A61N 2005/0627* (2013.01)

(58) Field of Classification Search
CPC ........ A61N 5/0625; A61N 5/10; A61N 5/103; A61N 5/1037; A61N 5/1038; A61N 5/1048; A61N 5/1064; A61N 5/1071; A61N 5/1075; A61N 2005/027; A61N 2005/0626; A61N 2005/0627; A61N 7/02; A61N 2007/0004; A61N 5/1031; A61F 7/00; A61F 2007/0088; A61F 2007/0089; A61F 2007/0093; A61F 2007/0095; A61F 2007/0096
See application file for complete search history.

(56) References Cited

U.S. PATENT DOCUMENTS

| 8,328,726 B2* | 12/2012 | Varghese ............... A61B 5/015 600/438 |
|---|---|---|
| 2004/0243200 A1 | 12/2004 | Turner |
| 2009/0312637 A1 | 12/2009 | Raju |
| 2012/0323599 A1 | 12/2012 | Bal |
| 2013/0131433 A1 | 5/2013 | Katscher |
| 2013/0267830 A1 | 10/2013 | Ojha |
| 2015/0011875 A1 | 1/2015 | Noordhoek |
| 2015/0165225 A1 | 6/2015 | Nadobny |

FOREIGN PATENT DOCUMENTS

| WO | 2010/051322 | 5/2010 |
|---|---|---|
| WO | 2013/164746 | 11/2013 |
| WO | 2014096993 | 6/2014 |
| WO | 2015/067786 | 5/2015 |
| WO | 2015085252 | 6/2015 |

OTHER PUBLICATIONS

Crezee, et al., "Thermoradiotherapy planning: Integration in routine clinical practice"; International Journal of Hyperthermia; vol. 32, No. 1, Jan. 2, 2016.

Wyatt, "Hyperthermia MRI Temperature Measurement: Evaluation of Measurement Stabilization Strategies for Extremity and Breast Tumors," Int J Hyperthermia. 2009; 25(6): 422-433.

Overgaard, "Formula to Estimate the Thermal Enhancement Ratio of a Single Simultaneous Hyperthermia and Radiation Treatment," Acru Radiologica Oncology 23 (1984) Fusc. 2-3.

* cited by examiner

ADAPTIVE TREATMENT PLANNING FOR HYPERTHERMIA-ENHANCED RADIATION THERAPY

CROSS REFERENCE TO RELATED APPLICATIONS

This application is the U.S. National Phase application under 35 U.S.C. § 371 of International Application No. PCT/EP2016/074609, filed Oct. 13, 2016, published as WO 2017/071965 on May 4, 2017, which claims the benefit of U.S. Provisional Patent Application No. 62/248,484 filed Oct. 30, 2015. These applications are hereby incorporated by reference herein.

FIELD OF THE INVENTION

The following generally relates to radiotherapy, and more particularly adaptive treatment planning for hyperthermia-enhanced radiation therapy (HT RT).

BACKGROUND OF THE INVENTION

Radiation therapy (RT) is a treatment in which ionizing radiation is applied to tissue to control or kill, e.g., malignant cancer cells. The amount of radiation (dose) prescribed in a treatment plan depends on the type and stage cells being treated. Radiation therapy plans have conventionally been fractionated, or spread out over time. For instance, the total dose of an RT treatment plan can be delivered over 30-35 fractions, with one (1) fraction per day, five (5) days per week, over six (6) weeks.

Hyperthermia (HT) refers to the use of high temperatures for therapeutic purposes. It is known that the application of HT prior to or during the delivery of RT to increase the target tissue temperature can serve to radiosensitize the targeted tissue. The HT temperature range for RT includes a temperature of forty-two and a half degrees Celsius (42.5° C.). The radiosensitizing effect is captured mathematically using the Thermal Enhancement Ratio (TER), which is defined as the following:

$$TER = \frac{\text{radiation dose to produce biologic effect X without hyperthermia}}{\text{radiation dose to produce biologic effect X with hyperthermia}}.$$

Hypofractionated radiotherapy regimes compress a conventional fractionated RT treatment into a shorter treatment span, e.g., one to two (1-2) weeks and five to ten (5-10) fractions, by increasing the amount of radiation delivered per fraction. Unfortunately, the higher dose per fraction increases the risk for normal tissue damage. Therefore, there is a need for an approach for a more conformal hypofractionated RT treatment approach.

SUMMARY OF THE INVENTION

Aspects described herein address the above-referenced problems and/or others.

In one aspect, a method includes generating a hyperthermia heat plan for tissue of interest, generating a hyperthermia adapted radiation therapy plan for the tissue of interest, controlling a heat source to deliver heat to the tissue of interest according to the hyperthermia heat plan, and controlling a radiation source of a radiation therapy system to deliver radiation to the tissue of interest according to the hyperthermia adapted radiation therapy plan.

In another aspect, a system includes a radiation treatment planner configured to generate a hyperthermia adapted radiation therapy plan for the tissue of interest, a radiation therapy system configured to deliver radiation in accordance with the hyperthermia adapted radiation therapy plan, and a hyperthermia heat delivery system configured to deliver heat in accordance with a hyperthermia plan.

In another aspect, a non-transitory computer readable medium is encoded with computer executable instructions, which when executed by a processor, causes the processor to: generate a hyperthermia heat plan for tissue of interest, generate a hyperthermia adapted radiation therapy plan for the tissue of interest, control a heat source to deliver heat to the tissue of interest according to the hyperthermia heat plan, and control a radiation source of a radiation therapy system to deliver radiation to the tissue of interest according to the hyperthermia adapted radiation therapy plan.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
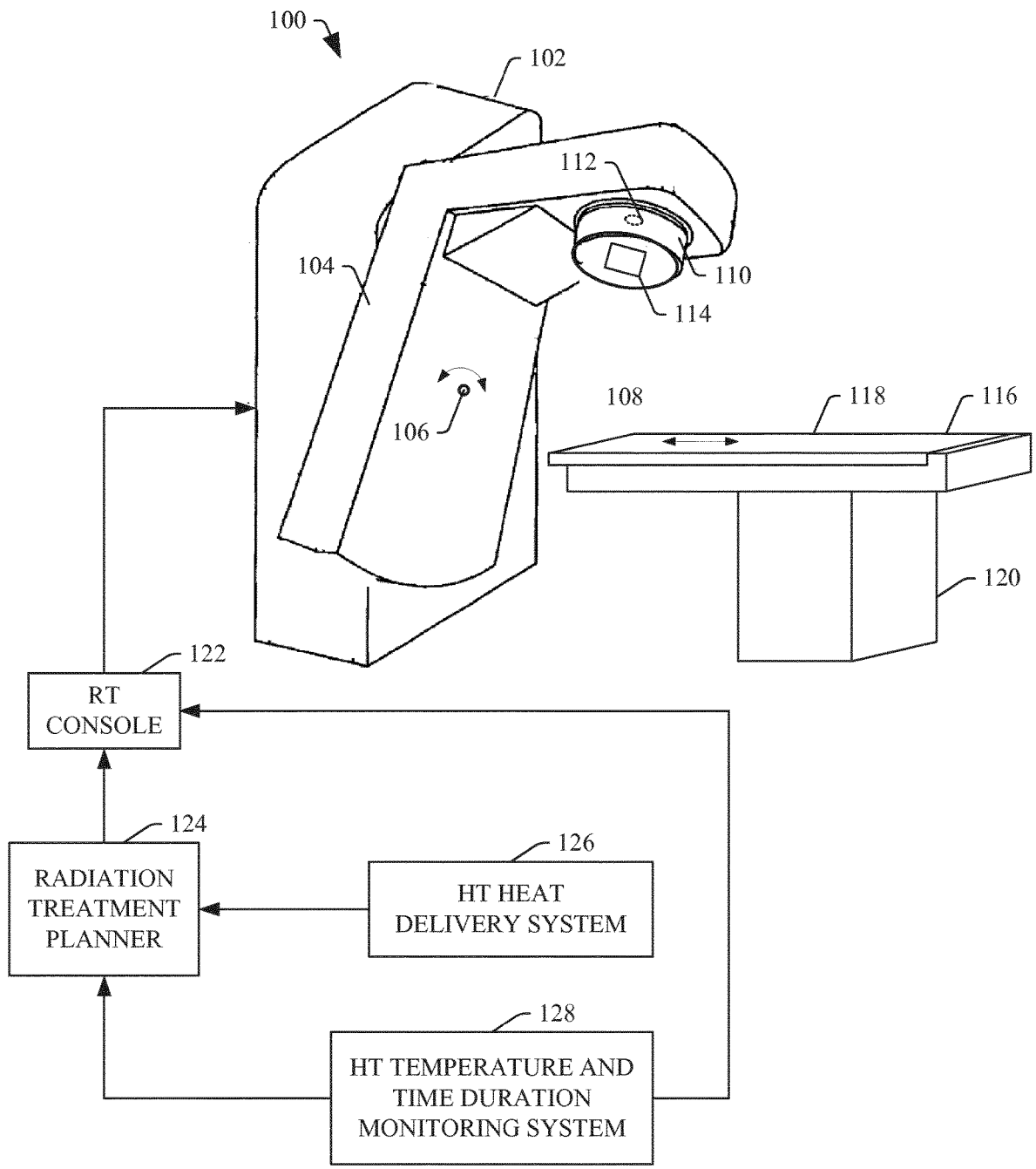
FIG. 1 schematically illustrates an example system including a radiation therapy system, a radiation treatment planner, a heat delivery system and a temperature and time duration monitoring system.

FIG. 1 schematically illustrates a radiation therapy system 100 such a linear accelerator, or linac. The radiation therapy system 100 includes a stationary gantry 102 and a rotating gantry 104, which is rotatably attached to the stationary gantry 102. The rotating gantry 104 rotates (e.g., 180°, etc.) with respect to a rotation axis 106 about a treatment region 108.

The stationary gantry 102 includes a treatment head 110 with a therapy (e.g., a megavolt (MV) radiation source 112 that delivers treatment radiation and a collimator 114 (e.g., a multi-leaf collimator) that can shape the radiation fields that exit the treatment head 110 into arbitrary shapes. The radiation source 112 rotates in coordination with the rotating gantry 104 about the treatment region 108. The collimator 114 includes a set of jaws that can move independently to shape a field.

A subject support 116 supports a portion of a subject in the treatment region 108. The subject support 116 includes a tabletop 118 configured to translate in and out of the treatment region 108 and a base 120. A computing system serves as an RT console 122, which is configured to control rotation of the rotating gantry 104 and delivery of treatment radiation by the megavolt radiation source 112 during a treatment. Software resident on the console 122 allows the operator to control the operation of the system 100.

A HT heat delivery system 126 is configured to apply heat before and/or concurrent with RT treatment radiation delivery. In this example, the HT heat delivery system 126 includes a high intensity focused ultrasound (HIFU) device. A HIFU device produces high intensity ultrasonic waves which are focused at the target tissue and which heat the target tissue. With this device, heating can be localized in the focal zone of the HIFU device without heating other tissue regions. Localizing can be desirable so as to not radiosensitize tissue outside of the target tissue, which would produce a toxic effect in the tissue outside of the tissue of interest due to the heat with no impact on the RT. Other heat sources are also contemplated herein.

The HT heat delivery system 126 and/or another computing device generate HT plans. In one instance, the HT plan is generated based on imaging data such as MR, CT, US, and/or other imaging data, and includes information such as placement of the HIFU transducer, control of transducer elements (e.g., controls heating depth and size of heating zone), heating duration, temperature used, target zone, etc. An example of creating a HIFU plan is described in US patent application publication US 2015/0011875A1, entitled "CT-HIFU system and/or method," and filed Feb. 21, 2013, the entirety of which is incorporated herein by reference.

A HT temperature and time duration monitoring system 128 is configured to monitor a temperature of the target tissue during and/or after HT, a time duration of the heat delivery, etc. In one instance, the HT temperature and time duration monitoring system 128 monitors the temperature based on imaging data such as MR, US, CT and/or other imaging data. In one instance, the HT temperature and time duration monitoring system 128 monitors the temperature on a voxel basis. In another instance, the HT temperature and time duration monitoring system 128 monitors the temperature on a group of voxels basis, such as a region of interest (ROI) and/or a contour.

An example MR thermometry based approach is discussed in Wyatt, "Hyperthermia MRI Temperature Measurement: Evaluation of Measurement Stabilization Strategies for Extremity and Breast Tumors," Int J Hyperthermia. 2009; 25(6): 422-433. An example US thermometry based approach is described in US patent application publication US 20090312637 A1, entitled "Ultrasound monitoring and feedback for magnetic hyperthermia", and field Jul. 12, 2006, the entirety of which is incorporated herein by reference. An example CT thermometry based approach is described in international patent application publication WO 2013164746 A1, entitled "Imaging Thermometry", and field Apr. 26, 2013, the entirety of which is incorporated herein by reference.

A radiation treatment planner 124 creates radiation treatment plans, including proton therapy plans, hypofractionated RT plans, and/or other plans. For sake of brevity and clarity, the following will be discussed in connection with a RT plan. As described in greater detail below, in one instance this includes adapting a non-HT RT plan (an RT plan in the absence of HT) based on a TER value and a corresponding ROI or contour to construct a HT-adapting RT plan and/or initially constructing the HT RT plans based on the TER value and the corresponding ROI or contour. The radiation treatment planner 124 is configured to do so for both sequential HT and RT delivery and concurrent HT and RT delivery. For sequential HT and RT delivery, the HT RT plan can take into account cooling down of the heated tissue after heat delivery. The resulting HT RT plan allows hypofractionated RT at a lower dose, relative to a fractionated RT plan without HT, while providing the same biological effect as the fractionated RT plan without HT. For example, the approach described herein can compress a conventional fractionated RT treatment into a shorter treatment span without increasing the risk of normal tissue damage.

The radiation treatment planner 124 can be implemented via a processor (e.g., microprocessor, central processing unit, controller, etc.) executing a computer readable instruction, which is encoded on non-transitory computer readable storage medium such a physical memory device. A computer readable instruction may also be carried by a carrier waver, a signal and/or other transitory medium. The radiation treatment planner 124 is shown separate from the RT console 122 in FIG. 1. In another embodiment, the radiation treatment planner 124 is a part of the RT console 122. In yet another embodiment, the radiation treatment planner 124 is distributed across the RT console 122 and at least one other computing device that is not part of the RT console 122.

FIGS. 2-5 illustrates non-limiting examples of the radiation treatment planner 124.

Figure 2:
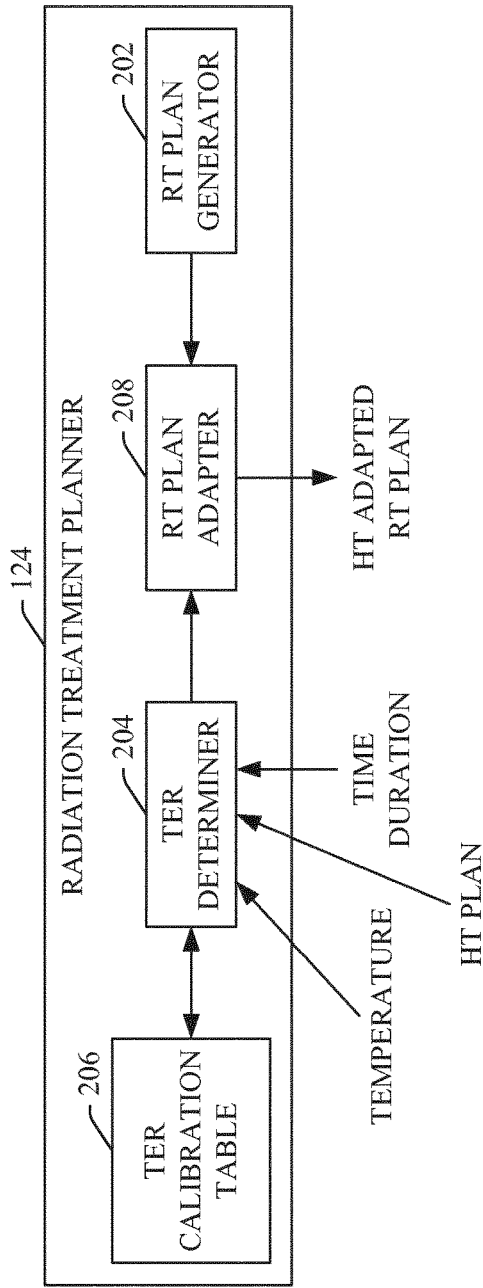
FIG. 2 schematically illustrates an example of the radiation treatment planner that employs a TER calibration table to convert RT plans to HT adapted RT plans.

In FIG. 2, the radiation treatment planner 124 includes an RT plan generator 202, which generates a non-HT RT plan. An example system for generating a non-HT RT is described in US patent application 20130267830 A1, entitled "Radiation therapy planning and follow-up system with large bore nuclear and magnetic resonance imaging or large bore ct and magnetic resonance imaging," and filed Dec. 13, 2001, the entirety of which is incorporated herein by reference.

A TER determiner 204 determines a TER for each voxel of interest and/or each group of voxels of interest (e.g., an ROI or a contour) based on the monitored temperature and heating time duration, the tissue type, etc. In this example, a TER calibration table 206 is predetermined and maps temperature and time duration to a TER value. Generally, a higher TER means a lower RT dose is needed in the presence of HT to realize the same biologic effect.

A RT plan adapter 208 adapts the non-HT RT plan based on the TER and the heated tissue to generate an HT adapted RT plan. In general, the RT plan is adapted in a localized region where active heating took place and includes scaling the doses of the non-HT RT plan by the TER value to generate HT RT doses for the HT adapted RT plan. In a variation, the RT plan may also be adapted to reduce a biologic effect in organs at risk. In one instance, the resulting HT adapted RT plan includes a lower dose for the target and immediate surrounding areas, while maintaining the original dose in regions further away from the target that have not been heated.

Figure 3:
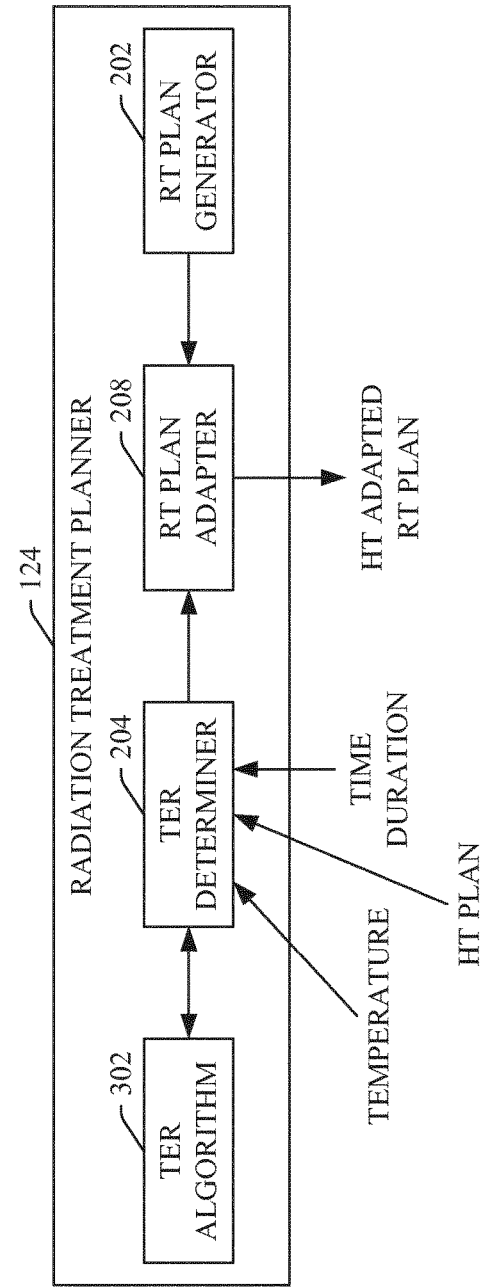
FIG. 3 schematically illustrates an example of the radiation treatment planner that calculates a TER value and converts RT plans to HT adapted RT plans based on the calculated TER.

FIG. 3 illustrates a variation of the radiation treatment planner 124 of FIG. 2. In this variation, the TER determiner 204 computes the TER value based on a TER algorithm 302. An example algorithm is discussed in Overgaard, "Formula to Estimate the Thermal Enhancement Ratio of a Single Simultaneous Hyperthermia and Radiation Treatment," Acru Radiologica Oncology 23 (1984) Fusc. 2-3.

Figure 4:
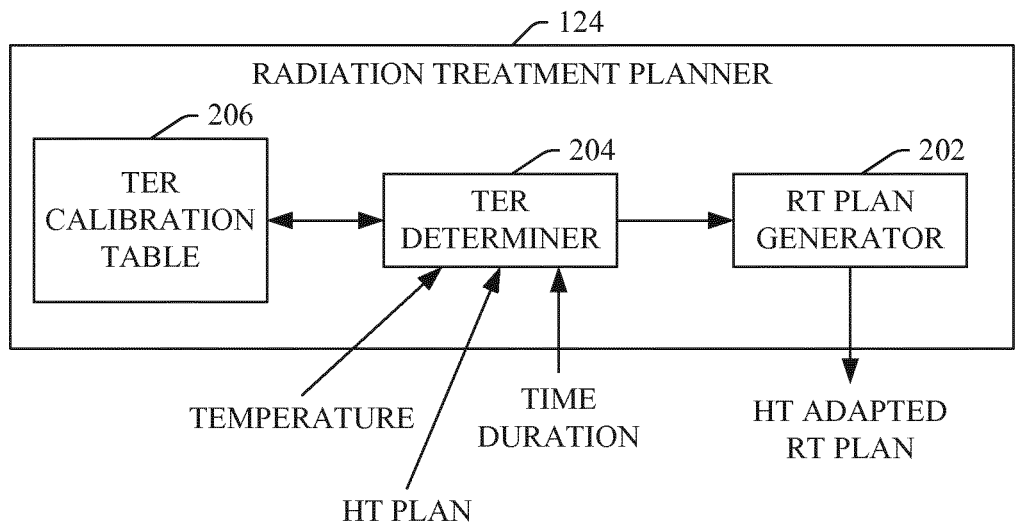
FIG. 4 schematically illustrates an example of the radiation treatment planner that employs a TER calibration table to create HT adapted RT plans.

FIG. 4 illustrates a variation of the radiation treatment planner 124 of FIG. 2 in which a non-HT RT plan is not first generated and then adapted, but instead, the HT adapted RT plan is directly generated by the RT plan generator 202 using the TER value from the TER calibration table 206.

Figure 5:
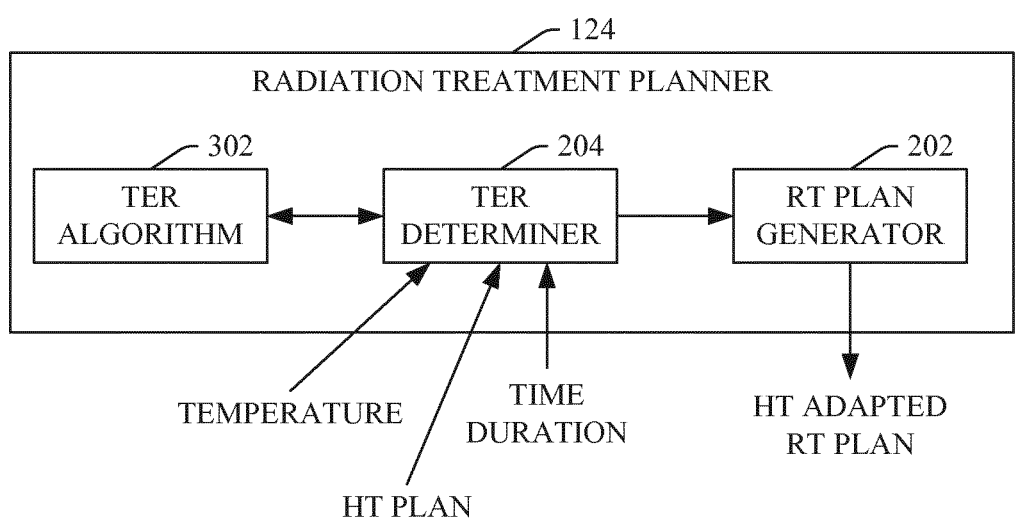
FIG. 5 schematically illustrates an example of the radiation treatment planner that calculates a TER value and creates HT adapted RT plans based on the calculated TER.

FIG. 5 illustrates a variation of the radiation treatment planner 124 of FIG. 3 in which a non-HT RT plan is not first generated and then adapted, but instead, the HT adapted RT plan is directly generated by the RT plan generator 202 using the calculated TER value.

Figure 6:
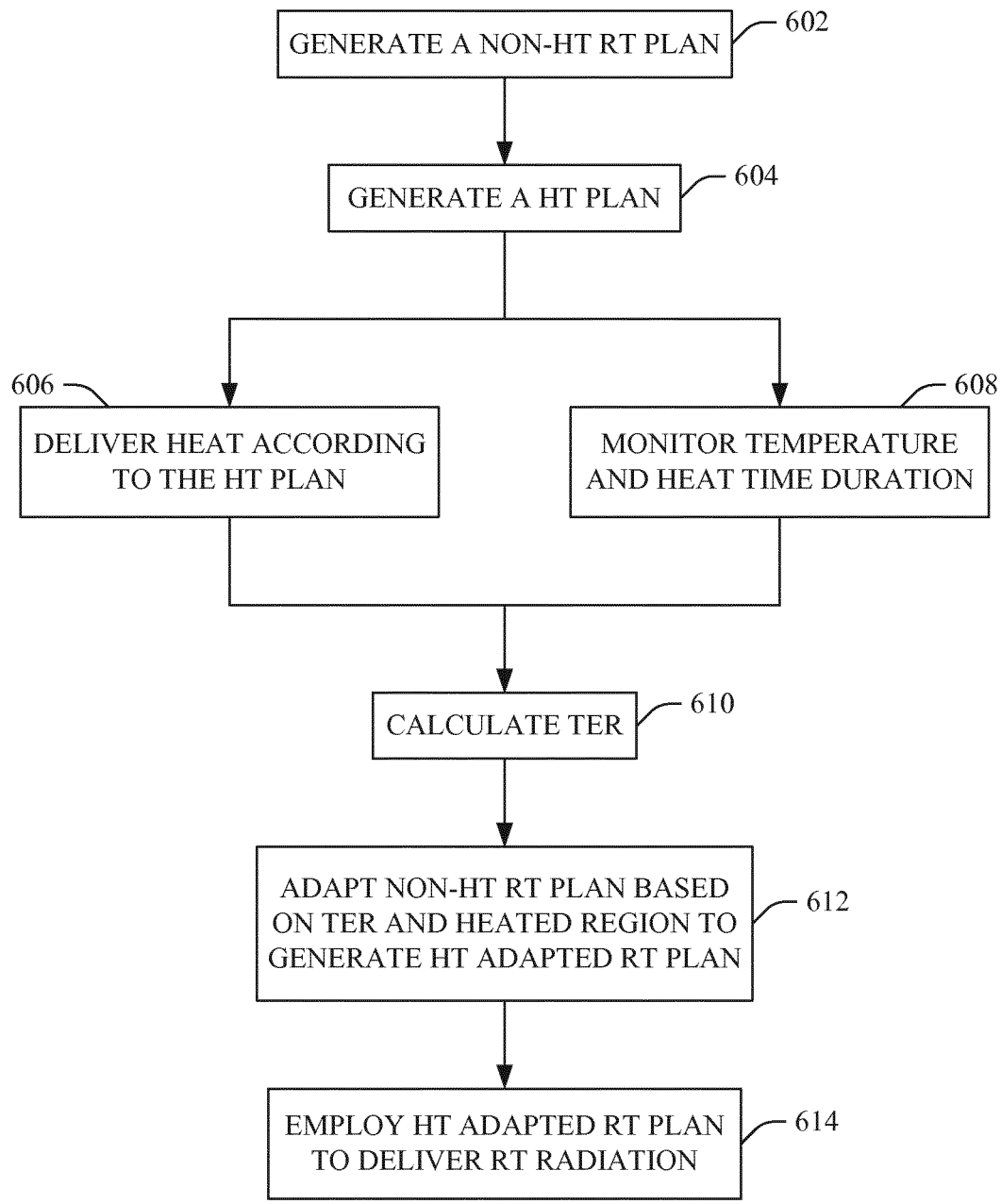
FIG. 6 schematically illustrates a method for creating a HT adapted RT plan for sequential HT and RT delivery by adapting a previously generated RT plan.
Figure 7:
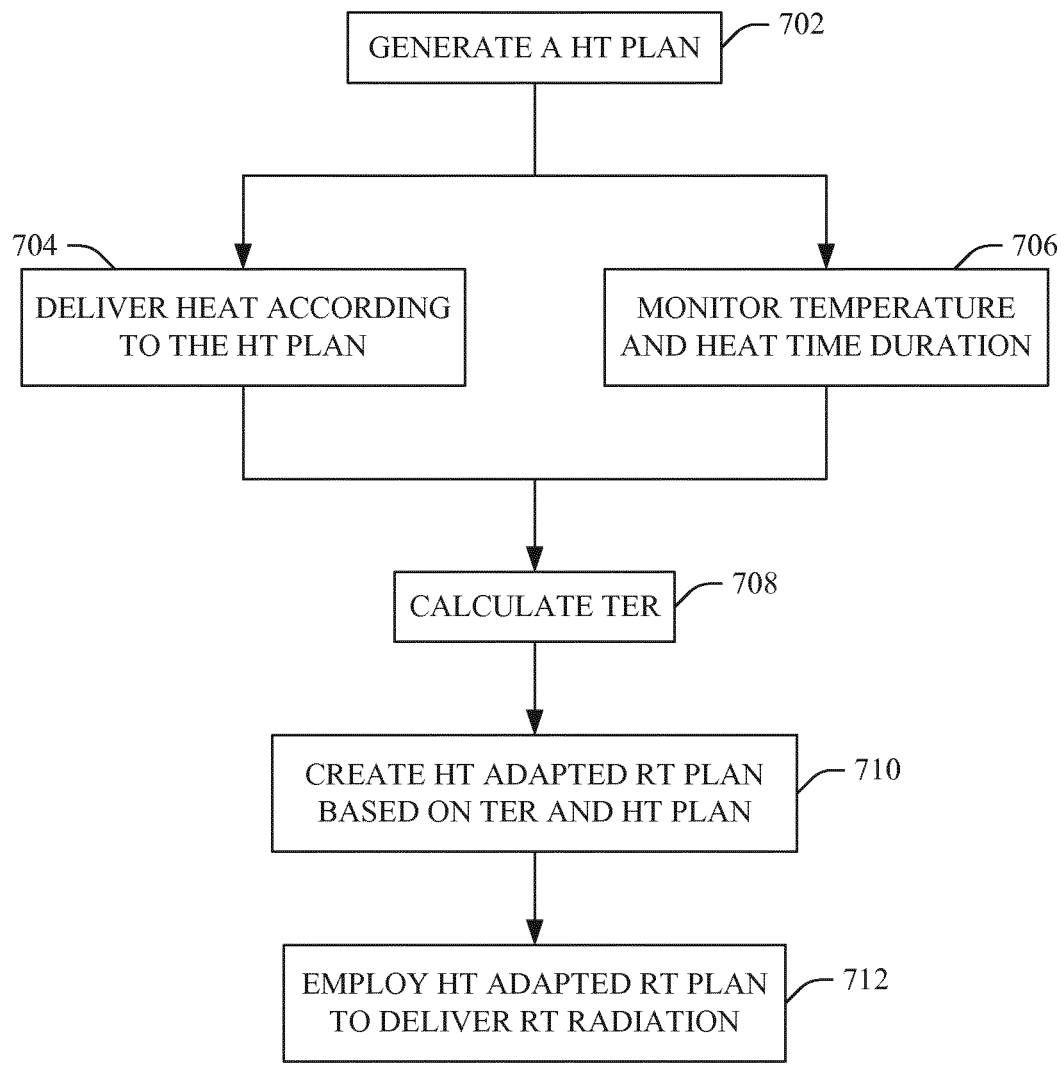
FIG. 7 schematically illustrates a method for creating a HT adapted RT plan for sequential HT and RT delivery without adapting a previously generated RT plan.
Figure 8:
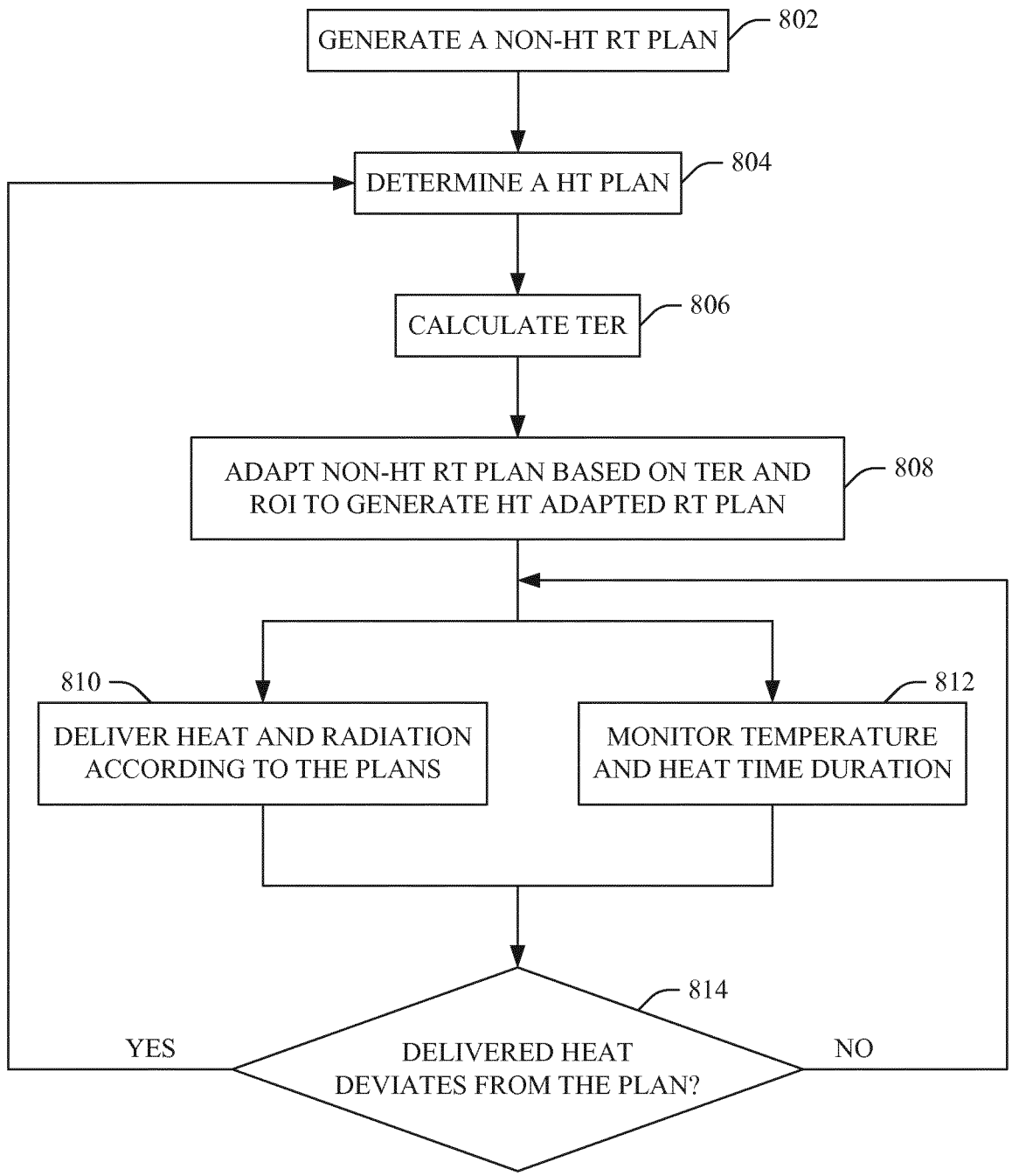
FIG. 8 schematically illustrates a method for creating a HT adapted RT plan for concurrent HT and RT delivery and adjusting the HT adapted RT plan based on HT delivery.

FIGS. 6-8 illustrate non-limiting methods for generating a HT adapted RT plan based on a TER value.

In FIG. 6, the HT adapted RT plan is created for sequential HT and RT delivery by adapting a previously generated non-HT RT plan.

At 602, a non-HT RT plan is generated.

At 604, a HT plan is generated.

At 606, the HT heat delivery system 126 delivers heat to a target region based on the HT plan.

At 608, concurrently with act 606, the temperature and time duration monitoring system 128 monitors HT delivery temperature and heating duration.

At 610, a TER is calculated based on the temperature and heat time duration.

At 612, the non-HT RT plan is adapted based on the TER and heated region, as described herein, and/or otherwise, to generate the HT adapted RT plan.

At 614, the HT adapted RT plan is employed by the RT console 122 to control radiation delivery.

In FIG. 7, the HT adapted RT plan is created for sequential HT and RT delivery by directly creating a HT adapted RT plan without a previously generated RT plan.

At 702, a HT plan is generated.

At 704, the HT heat delivery system 126 delivers heat to a target region based on the HT plan.

At 706, concurrently with act 606, the temperature and time duration monitoring system 128 monitors HT delivery temperature and heating duration.

At 708, a TER is calculated based on the temperature and heat time duration.

At 710, the HT adapted RT plan is generated based on the TER and the heated region, as described herein, and/or otherwise, to generate the HT adapted RT plan.

At 712, the HT RT plan is employed by the RT console 122 to control radiation delivery.

In FIG. 8, the HT adapted RT plan is created for concurrent HT and RT delivery and later adjusted based on HT delivery if needed.

At 802, a non-HT RT plan is generated.

At 804, a HT plan is generated.

At 806, a TER is calculated based on planned temperature and heat delivery time duration.

At 808, the non-HT RT plan is adapted based on the TER and the tissue of interest to generate the HT adapted RT plan.

At 810, radiation and heat delivery according to the HT adapted RT plan and the HT plan concurrently commences.

At 812, concurrently with act 810, the temperature and time duration monitoring system 128 monitors HT delivery temperature and heating duration.

At 814, the monitored temperature is compared with the planned temperature. It is to be appreciated that heat delivery may deviate from the plan, e.g., as necessitated by tissue motion, etc.

If the monitored temperature deviates from the planned temperature by more than a predetermined tolerance, then the temperature and time duration monitoring system 128 conveys a signal to the RT console 122, which causes the console 122 to terminate or pause radiation delivery, and acts 804 to 814 are repeated, where a new TER is calculated. Alternatively, the HT adapted RT plan is dynamically adjusted, e.g., based on a predicative change in heat delivery. If the monitored temperature is within the tolerance, acts 810 to 814 are repeated.

Figure 9:
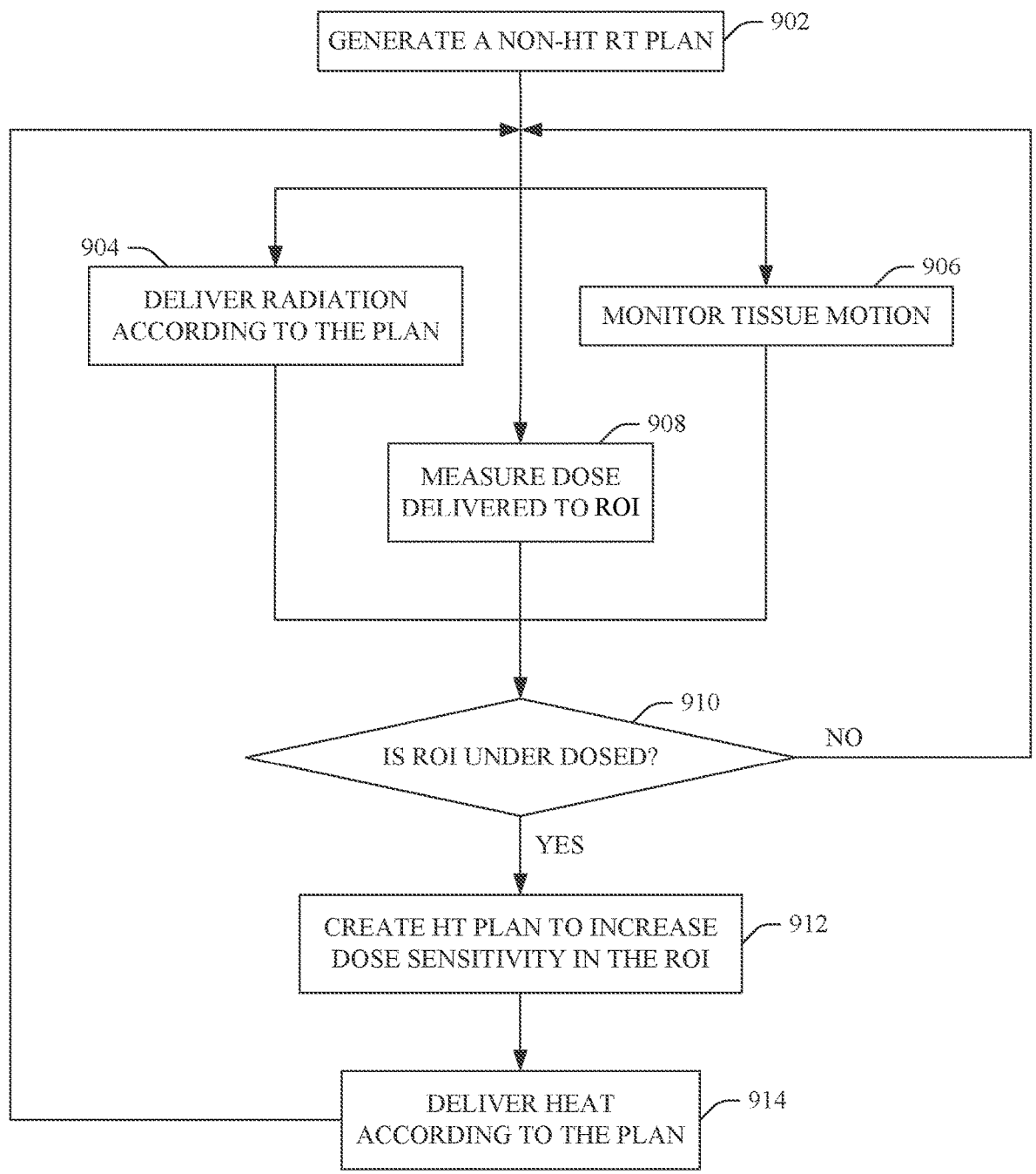
FIG. 9 illustrates a method for selectively creating a HT plan in connection with sequential RT and HT delivery.

FIG. 9 illustrates a method for selectively creating a HT plan in connection with sequential RT and HT delivery.

At 902, a non-HT RT plan is generated.

At 904, radiation is delivered according to the non-HT RT plan.

At 906, concurrently with act 904, tissue motion is tracked. This can be achieved via real time ultrasound and/or otherwise. A non-limiting example is described in application serial number PCT/IB2013/058588, publication number WO2014096993 A1, entitled "Real-time adaptive dose computation radiation therapy," and filed Sep. 17, 2013, the entirety of which is incorporated herein by reference.

At 908, concurrently with acts 904 and 906, the dose delivered to the region of interest (ROI) is measured. A non-limiting example is described in application serial number PCT/IB2013/058588, publication number WO2014096993 A1, entitled "Real-time adaptive dose computation radiation therapy," and filed Sep. 17, 2013.

At 910, it is determined whether the ROI is under dosed based on the non-HT RT plan and the measured dose.

If it is determined the ROI is under dosed, at 912 a HT plan is created, at 914 heat is delivered according to the HT plan, and acts 904-910 are repeated.

If it is determined the ROI is not under dosed, acts 904-910 are repeated.

The method herein may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   generating a hyperthermia heat plan for tissue of interest;
   generating a hyperthermia adapted radiation therapy plan for the tissue of interest;
   before delivering heat to tissue of interest according to the hyperthermia heat plan: generating a non-hyperthermia radiation therapy plan; and generating the hyperthermia adapted radiation therapy plan by adapting the non-hyperthermia radiation therapy plan;
   controlling a heat source to deliver heat to the tissue of interest according to the hyperthermia heat plan; and controlling a radiation source of a radiation therapy system to deliver radiation to the tissue of interest according to the hyperthermia adapted radiation therapy plan.

2. The method of claim 1, further comprising:
monitoring a temperature of the tissue of interest and a time duration of the heat delivery; and
generating the hyperthermia adapted radiation therapy plan by adapting the non-hyperthermia radiation therapy plan based on the temperature of the tissue of interest and the time duration of the heat delivery.

3. The method of claim 2, further comprising:
determining a thermal enhancement ratio based on the monitored temperature of the tissue of interest and the time duration of the heat delivery; and
generating the hyperthermia adapted radiation therapy plan by adapting the non-hyperthermia radiation therapy plan based on the thermal enhancement ratio and the tissue of interest.

4. The method of claim 3, wherein generating the hyperthermia adapted radiation therapy plan includes scaling a radiation dose value of the non-hyperthermia radiation therapy plan for the tissue of interest by the thermal enhancement ratio.

5. The method of claim 1, further comprising:
monitoring a temperature of the tissue of interest and a time duration of the heat delivery; and
generating the hyperthermia adapted radiation therapy plan based on the temperature of the tissue of interest and the time duration of the heat delivery.

6. The method of claim 5, further comprising:
determining a thermal enhancement ratio based on the temperature of the tissue of interest and the time duration of the heat delivery; and
generating the hyperthermia adapted radiation therapy plan based on the thermal enhancement ratio and the tissue of interest.

7. The method of claim 1, wherein the heat and the radiation are concurrently delivered.

8. The method of claim 7, further comprising, before generating the hyperthermia adapted radiation therapy plan for the tissue of interest:
generating a non-hyperthermia radiation therapy plan;
determining a thermal enhancement ratio based on a planned temperature and a planned time duration of heat delivery in the hyperthermia heat plan; and
generating the hyperthermia adapted radiation therapy plan by adapting the non-hyperthermia radiation therapy plan based on the thermal enhancement ratio and the tissue of interest.

9. The method of claim 8, further comprising:
monitoring a temperature of the tissue of interest and a time duration of the heat delivery during heat delivery;
comparing the monitored temperature and the planned temperature;
determining a delivered HT pattern based on a deviation between the monitored temperature and the planned temperature;
generating a second hyperthermia heat plan;
determining a second thermal enhancement ratio based on the delivered HT pattern;
generating a second hyperthermia adapted radiation therapy plan based on the second thermal enhancement ratio and the tissue of interest;
controlling the heat source to deliver heat to the tissue of interest according to the second hyperthermia heat plan; and controlling the radiation source of a radiation therapy system to deliver radiation to the tissue of interest according to the second hyperthermia adapted radiation therapy plan.

10. The method of claim 1, further comprising, before generating a hyperthermia heat plan for tissue of interest:
controlling the radiation source of the radiation therapy system to deliver radiation to the tissue of interest according to non-hyperthermia radiation therapy plan;
monitoring a motion of the tissue of interest;
monitoring a radiation dose applied to the tissue of interest;
generating the hyperthermia heat plan for the tissue of interest in response to the applied radiation dose deviating from dose planned in the non-hyperthermia radiation therapy plan; and
controlling the heat source to deliver heat to the tissue of interest according to the hyperthermia heat plan.

11. The method of claim 1, wherein the hyperthermia adapted radiation therapy plan includes a fractionated radiation therapy plan.

12. The method of claim 1, wherein the hyperthermia adapted radiation therapy plan includes a hypofractionated radiation therapy plan.

13. A system, comprising:
a radiation treatment planner configured to generate a hyperthermia adapted radiation therapy plan for tissue of interest based on a thermal enhancement ratio;
a radiation therapy system configured to deliver radiation in accordance with the hyperthermia adapted radiation therapy plan; and
a hyperthermia heat delivery system configured to deliver heat in accordance with a hyperthermia plan, wherein before delivering heat to tissue of interest according to the hyperthermia plan, the radiation treatment planner is configured to: generate a non-hyperthermia radiation therapy plan; and generate the hyperthermia adapted radiation therapy plan by adapting the non-hyperthermia radiation therapy plan.

14. The system of claim 13, wherein the radiation therapy system is configured to deliver the radiation after the hyperthermia heat delivery system delivers the heat, and further comprising:
a hyperthermia temperature and time duration monitoring system configured to monitor a temperature and heat delivery time duration,
wherein the radiation treatment planner generates a non-hyperthermia radiation therapy plan before the heat is delivered to the tissue of interest, monitors a temperature of the tissue of interest and a time duration of the heat delivery, determines the thermal enhancement ratio based on the temperature of the tissue of interest and the time duration of the heat delivery, and generates the hyperthermia adapted radiation therapy plan by adapting the non-hyperthermia radiation therapy plan based on the thermal enhancement ratio and the tissue of interest.

15. The system of claim 13, wherein the radiation therapy system is configured to deliver the radiation after the hyperthermia heat delivery system delivers the heat, and further comprising:
a hyperthermia temperature and time duration monitoring system configured to monitor a temperature and heat delivery time duration,
wherein the radiation treatment planner determines the thermal enhancement ratio based on the temperature of the tissue of interest and the time duration of the heat delivery and generates the hyperthermia adapted radiation therapy plan based on the thermal enhancement ratio and the tissue of interest.

16. The system of claim 13, wherein the radiation therapy system is configured to deliver the radiation concurrently with the hyperthermia heat delivery system delivering the heat, wherein the radiation treatment planner generates a non-hyperthermia radiation therapy plan, generates the thermal enhancement ratio based on a planned temperature of the tissue of interest and a planned time duration of the heat delivery, generates the hyperthermia adapted radiation therapy plan by adapting the non-hyperthermia radiation therapy plan based on the thermal enhancement ratio and the tissue of interest.

17. The system of claim 16, wherein the radiation therapy system is configured to deliver the radiation concurrently with the hyperthermia heat delivery system delivering the heat, and further comprising:
a hyperthermia temperature and time duration monitoring system configured to monitor a temperature and heat delivery time duration, wherein the radiation treatment planner compares the monitored temperature and the planned temperature, determines a delivered HT pattern based on a deviation between the monitored temperature and the planned temperature, determines a second thermal enhancement ratio based on the delivered HT pattern, and generates a second hyperthermia adapted radiation therapy plan based on the second thermal enhancement ratio and the tissue of interest, and wherein the radiation therapy system is configured to deliver radiation in accordance with the second hyperthermia adapted radiation therapy plan, and the hyperthermia heat delivery system is configured to deliver heat in accordance with the second hyperthermia plan.

18. The system of claim 13, wherein the radiation treatment planner is configured to generate a non-hyperthermia radiation therapy plan for the tissue of interest and the radiation therapy system is configured to deliver radiation in accordance with the non-hyperthermia radiation therapy plan, and further comprising:
a motion monitor configured to monitor a motion of the tissue of interest;
a radiation dose determiner configured to determine an applied radiation dose applied to the tissue of interest,
wherein the radiation therapy system is configured to generate the hyperthermia heat plan for the tissue of interest in response to the applied radiation dose deviating from dose planned in the non-hyperthermia radiation therapy plan, and the hyperthermia heat delivery system is configured to deliver heat in accordance with the hyperthermia plan before the delivery of further radiation.

19. A non-transitory computer readable medium encoded with computer executable instructions, which when executed by a processor, causes the processor to:
generate a hyperthermia heat plan for tissue of interest;
generate a hyperthermia adapted radiation therapy plan for the tissue of interest based on a thermal enhancement ratio;
before delivering heat to tissue of interest according to the hyperthermia plan, generate a non-hyperthermia radiation therapy plan; and generate the hyperthermia adapted radiation therapy plan by adapting the non-hyperthermia radiation therapy plan;
control a heat source to deliver the heat to the tissue of interest according to the hyperthermia heat plan; and
control a radiation source of a radiation therapy system to deliver radiation to the tissue of interest according to the hyperthermia adapted radiation therapy plan.

20. The non-transitory computer readable medium of claim 19, wherein the computer executable instructions, which when executed by the processor, further cause the processor to:
monitor a temperature of the tissue of interest and a time duration of the heat delivery;
determine the thermal enhancement ratio based on the temperature of the tissue of interest and the time duration of the heat delivery; and
generate the hyperthermia adapted radiation therapy plan by adapting the non-hyperthermia radiation therapy plan based on the thermal enhancement ratio and the tissue of interest.

21. The non-transitory computer readable medium of claim 19, wherein the computer executable instructions, which when executed by the processor, further cause the processor to:
monitor a temperature of the tissue of interest and a time duration of the heat delivery;
determine the thermal enhancement ratio based on the temperature of the tissue of interest and the time duration of the heat delivery; and
generate the hyperthermia adapted radiation therapy plan based on the thermal enhancement ratio and the tissue of interest.

22. The non-transitory computer readable medium of claim 19, wherein the computer executable instructions, which when executed by the processor, further cause the processor to:
determine the thermal enhancement ratio based on a planned temperature and a planned time duration of heat delivery in the hyperthermia heat plan; and
generate the hyperthermia adapted radiation therapy plan by adapting the non-hyperthermia radiation therapy plan based on the thermal enhancement ratio and the tissue of interest.

23. The non-transitory computer readable medium of claim 22, wherein the computer executable instructions, which when executed by the processor, further cause the processor to:
monitor a temperature of the tissue of interest and a time duration of the heat delivery during heat delivery;
compare the monitored temperature and the planned temperature; and
determine a delivered hyperthermia pattern based on a deviation between the monitored temperature and the planned temperature;
generate a second hyperthermia heat plan;
determine a second thermal enhancement ratio based on the delivered hyperthermia pattern;
generate a second hyperthermia adapted radiation therapy plan based on the second thermal enhancement ratio and the tissue of interest;
control the heat source to deliver heat to the tissue of interest according to the second hyperthermia heat plan; and
control the radiation source of a radiation therapy system to deliver radiation to the tissue of interest according to the second hyperthermia adapted radiation therapy plan.

24. The non-transitory computer readable medium of claim 19, wherein the computer executable instructions, which when executed by the processor, further cause the processor to:

generate a non-hyperthermia radiation therapy plan;
control the radiation source of the radiation therapy system to deliver radiation to the tissue of interest according to non-hyperthermia radiation therapy plan;
monitor a motion of the tissue of interest;
monitor a radiation dose applied to the tissue of interest;
generate the hyperthermia heat plan for the tissue of interest in response to the applied radiation dose deviating from dose planned in the non-hyperthermia radiation therapy plan; and
control the heat source to deliver heat to the tissue of interest according to the hyperthermia heat plan.

* * * * *